US011793526B2

(12) United States Patent
Alambeigi et al.

(10) Patent No.: US 11,793,526 B2
(45) Date of Patent: Oct. 24, 2023

(54) STEERABLE DRILL FOR MINIMALLY-INVASIVE SURGERY

(71) Applicant: THE JOHNS HOPKINS UNIVERSITY, Baltimore, MD (US)

(72) Inventors: Farshid Alambeigi, Baltimore, MD (US); Mehran Armand, Fulton, MD (US)

(73) Assignee: The Johns Hopkins University, Baltimore, MD (US)

( * ) Notice: Subject to any disclaimer, the term of this patent is extended or adjusted under 35 U.S.C. 154(b) by 248 days.

(21) Appl. No.: 16/490,751

(22) PCT Filed: Jan. 3, 2018

(86) PCT No.: PCT/US2018/012162
§ 371 (c)(1),
(2) Date: Sep. 3, 2019

(87) PCT Pub. No.: WO2018/160269
PCT Pub. Date: Sep. 7, 2018

(65) Prior Publication Data
US 2020/0000480 A1   Jan. 2, 2020

Related U.S. Application Data

(60) Provisional application No. 62/466,424, filed on Mar. 3, 2017.

(51) Int. Cl.
*A61B 17/16* (2006.01)
*A61B 17/00* (2006.01)

(52) U.S. Cl.
CPC .... *A61B 17/1642* (2013.01); *A61B 17/00234* (2013.01); *A61B 17/1617* (2013.01);
(Continued)

(58) Field of Classification Search
CPC ...................... A61B 17/16–17/1697
See application file for complete search history.

(56) References Cited

U.S. PATENT DOCUMENTS 6,096,042 A    8/2000  Herbert
8,002,733 B2*  8/2011  Kraft ................ A61B 10/025
                                                    604/35

(Continued)

OTHER PUBLICATIONS

Watanabe, et al., Development of a "steerable drill" for ACL reconstruction to create the arbitrary trajectory of a bone tunnel. Intelligent Robots and Systems (IROS), 2011 IEEE/RSJ International Conference on. Dec. 5, 2011; 955-960.

(Continued)

*Primary Examiner* — Zade Coley
(74) *Attorney, Agent, or Firm* — JOHNS HOPKINS TECHNOLOGY VENTURES

(57) ABSTRACT

An embodiment in accordance with the present invention provides a continuum dexterous manipulator (CDM) with a specially designed flexible tool, to be used as a handheld or robotic steerable device for treatment of hard-tissue-related diseases. The CDM of the present invention works well in treatment of soft and sticky material (similar to a lesion) as well as milling the hard tissues (e.g. sclerotic liner of osteolytic lesions) and bone tumors. The present invention is also directed to flexible drilling tools as well as characterization and evaluation of integrating these tools with the CDM in curved-drilling of hard bone towards treatment of hard tissue related diseases (e.g. osteonecrosis or pelvic fracture). The present invention can also include use of various types of drill geometries, aspiration and irrigation, and endoscope view in curved-drilling and trajectory planning.

21 Claims, 15 Drawing Sheets

(52) U.S. Cl.
CPC ...... *A61B 17/1631* (2013.01); *A61B 17/1626* (2013.01); *A61B 2017/003* (2013.01)

(56) References Cited

U.S. PATENT DOCUMENTS

| | | | |
|---|---|---|---|
| 8,590,636 B2 | 11/2013 | Menger | |
| 8,685,031 B2 | 4/2014 | Kleiner et al. | |
| 9,398,962 B2* | 7/2016 | Steinberg | A61F 2/38 |
| 9,474,536 B2* | 10/2016 | Carrison | A61B 17/1671 |
| 2003/0097133 A1* | 5/2003 | Green | A61B 17/164 606/80 |
| 2003/0225364 A1* | 12/2003 | Kraft | A61B 17/1615 604/35 |
| 2004/0249277 A1* | 12/2004 | Kato | A61M 25/0012 606/108 |
| 2009/0270862 A1* | 10/2009 | Arcenio | A61B 17/1671 606/79 |
| 2010/0160867 A1 | 6/2010 | Miller et al. | |
| 2012/0245692 A1* | 9/2012 | Steinberg | A61B 34/30 623/17.16 |
| 2013/0043076 A1 | 2/2013 | Larronde et al. | |
| 2014/0316434 A1* | 10/2014 | Simaan | A61B 34/30 606/130 |
| 2014/0324052 A1* | 10/2014 | Carrison | A61B 17/1617 606/80 |
| 2014/0330432 A1* | 11/2014 | Simaan | B25J 9/1625 700/250 |
| 2015/0066033 A1* | 3/2015 | Jorgensen | A61B 34/71 606/170 |
| 2015/0257800 A1* | 9/2015 | Harshman | A61B 17/1717 606/62 |
| 2016/0000991 A1* | 1/2016 | Kraft | A61M 1/85 604/28 |
| 2016/0166341 A1* | 6/2016 | Iordachita | A61B 34/35 606/130 |

OTHER PUBLICATIONS

Lieberman, et al., Osteonecrosis of the hip: management in the 21st century. Instr Course Lect. 2003;52:337-55.
Soohoo, et al.. Cost-effectiveness analysis of core decompression. J Arthroplasty. Aug. 2006;21(5):670-81.
Lee, et al., Elevated intraosseous pressure in the intertrochanteric region is associated with poorer results in osteonecrosis of the femoral head treated by multiple drilling. J Bone Joint Surg Br. Jul. 2008;90(7):852-7.
Nishii, et al., Significance of lesion size and location in the prediction of collapse of osteonecrosis of the femoral head: a new three-dimensional quantification using magnetic resonance imaging. J Orthop Res. Jan. 2002;20(1):130-6.
Murphy, et al., Design and kinematic characterization of a surgical manipulator with a focus on treating osteolysis. Robotica. Sep. 2014;32(6):835-850.
Alaambeigi, et al., Control of the coupled motion of a 6 DoF robotic arm and a continuum manipulator for the treatment of pelvis osteolysis. Conf Proc IEEE Eng Med Biol Soc. 2014;2014:6521-5.
Alambeigi, et al., Design and characterization of a debriding tool in robot-assisted treatment of osteolysis. Robotics and Automation (ICRA), 2016 IEEE International Conference on. Jun. 2016; 5664-5669.
Alambeigi, et al., Toward robot-assisted hard osteolytic lesion treatment using a continuum manipulator. Engineering in Medicine and Biology Society (EMBC), 2016 IEEE 38th Annual International Conference of the. Oct. 2016; 5103-5106.
Hufner, et al., Accuracy study of computer-assisted drilling: the effect of bone density, drill bit characteristics, and use of a mechanical guide. J Orthop Trauma. May-Jun. 2005;19(5):317-22.
Pandey, et al., Drilling of bone: A comprehensive review. J Clin Orthop Trauma. Mar. 2013;4(1):15-30.
Saha, et al., Surgical drilling: design and performance of an improved drill. J Biomech Eng. Aug. 1982;104(3):245-52.
Wang, et al., Experimental investigations and finite element simulation of cutting heat in vibrational and conventional drilling of cortical bone. Med Eng Phys. Nov. 2014;36(11):1408-15.
Wang, et al., Experimental Investigations on Microcracks in Vibrational and Conventional Drilling of Cortical Bone. J Nanomaterials. 2013; 6.
Khadem, et al., Ultrasound-Guided Model Predictive Control of Needle Steering in Biological Tissue. J Medical Robotics Research 2016; 1: 1640007.
Navarro-Alarcon, et al., Automatic 3-D Manipulation of Soft Objects by Robotic Arms With an Adaptive Deformation Model. IEEE Transactions on Robotics. Apr. 2016; 32(2):429-441.
Penney, et al., A comparison of similarity measures for use in 2-D-3-D medical image registration. IEEE Trans Med Imaging Aug. 1998;17(4):586-95.
Sefati, et al., FBG-Based Large Deflection Shape Sensing of a Continuum Manipulator: Manufacturing Optimization. Sensors, 2016 IEEE. Jan. 2017.

* cited by examiner

STEERABLE DRILL FOR MINIMALLY-INVASIVE SURGERY

CROSS-REFERENCE TO RELATED APPLICATIONS

This application is a 35 U.S.C. § 371 U.S. national entry of International Application PCT/US2018/012162, having an international filing date of Jan. 3, 2018, which claims the benefit of U.S. Provisional Application No. 62/466,424, filed Mar. 3, 2017, the content of each of the aforementioned applications is herein incorporated by reference in their entirety.

GOVERNMENT SUPPORT

This invention was made with government support under R01EB016703-01A1 awarded by the National Institutes of Health. The government has certain rights in the invention.

FIELD OF THE INVENTION

The present invention relates generally to medical devices. More particularly, the present invention relates to a steerable device for treatment of hard-tissue-related diseases and for minimally-invasive surgery.

BACKGROUND OF THE INVENTION

More than 20,000 patients are diagnosed each year with osteonecrosis of the femoral head, most of them aged between 20 and 50 years. Delayed treatment of these patients leads to total hip arthroplasty (THA) surgery. Osteonecrosis disrupts blood supply to the femoral head which causes pain and eventually leads to collapse of the subchondral bone. To reduce the pressure in the femoral head, enhance vascular flow, and alleviate pain, core decompression was developed more than three decades ago. It is the most common early-stage treatment of osteonecrosis to preserve the femoral head from total hip replacement.

Currently, core decompression to treat osteonecrosis is performed with two techniques. It removes the lesion area by drilling either a hole with 8 to 12 mm diameter or multiple 3 mm holes in the femoral head, as illustrated in FIG. 1. After debriding, a bone graft injection into the core fills and stabilizes the femoral head. However, due to individual variation in distributions, sizes and shapes of the necrotic lesion, utilizing conventional rigid tools limit accessibility and debridement of the entire lesion. This results in incomplete removal of the necrotic bone and potential collapse or damage to the cartilage overlying the femoral head. The ideal surgical outcome would be entire lesion removal without any compromise to normal bone. While osteonecrosis is described herein there are a number of conditions and treatments that require drilling of bone or other hard tissues, such as arthroplasty of hip or knee, pelvic osteotomy, and spine screw insertion.

Therefore, it would be advantageous to provide a steerable device for treatment of hard-tissue-related diseases for minimally-invasive surgery.

SUMMARY OF THE INVENTION

The foregoing needs are met, to a great extent, by the present invention, wherein in one aspect a drilling device including a steerable mechanism comprising a flexible portion with a controllable bending angle. The steerable mechanism further includes a flexible cable configured to actuate the controllable bending angle. The steerable mechanism defines an inner lumen. The drilling device includes a cutting tool configured to be disposed through the inner lumen of the steerable mechanism. The drilling device also includes a driving mechanism having a control mechanism configured to provide control of the controllable bending angle of the steerable mechanism.

In accordance with an aspect of the present invention, the driving mechanism includes a housing. A motor is disposed within the housing of the driving mechanism. A battery is also disposed within the housing of the driving mechanism. The driving mechanism includes a switch for engaging a rotational drilling action of the steerable mechanism. The control mechanism can take the form of a joystick or directional control buttons. The drilling device further includes robotic control of the steerable mechanism. The driving mechanism includes a control for speed of the rotational drilling action of the steerable mechanism. The steerable mechanism takes the form of a continuum dexterous manipulator (CDM). The CDM is formed from a metal such as titanium or nitinol. The controllable bending angle is controlled by pulling on the flexible cable. The steerable mechanism defines a second lumen through which an endoscope can be disposed. The cutting tool can take the form of a ball end-mill. The steerable mechanism further includes notches cut along its length to facilitate bending. The steerable mechanism defines a plurality of channels through which a plurality of flexible cables are disposed for control of the steerable mechanism. The plurality of cables are actuated to provide movement of the steerable mechanism. The cutting tool includes a flexible distal end. The cutting tool is formed from a metal. The cutting tool includes a quick connect mechanism.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a continuum dexterous manipulator (CDM) with a specially designed flexible drilling tool, to be used as a steerable device for treatment of hard-tissue-related diseases. The CDM of the present invention works well in treatment of soft and sticky material (similar to a lesion) as well as milling the hard sclerotic liner of osteolytic lesions. The present invention is also directed to flexible drilling tools as well as characterization and evaluation of integrating these tools with the CDM in curved-drilling of hard bone towards treatment of the bone lesion (e.g. osteonecrosis of the femoral head or treatment of pelvic fracture) and tumor. The most important parameters are drill geometry (e.g. drill diameter, drill point angle, helix angle and etc.) as well as the drilling parameters (e.g. rotational speed of the drill, feeding speed/force of the drill, and etc.). The present invention can also include use of two different drill geometries in curved-drilling and trajectory planning.

The present invention can serve many purposes depending on the type of tool passed through the open lumen of the continuum manipulator. The steerable device can be used as a cutting device (i.e. a steerable drilling or milling device); a steerable endoscope; a steerable cutting device together with an endoscope; a steerable injector to fill the drilled tunnel with bone cement. The steerable device can be used for treatment of osteonecrosis or bone augmentation of the femoral head, among other uses such as treatments that require drilling of bone or other hard tissues, such as arthroplasty of hip or knee, pelvic osteotomy, and spine screw insertion.

Figure 2A:
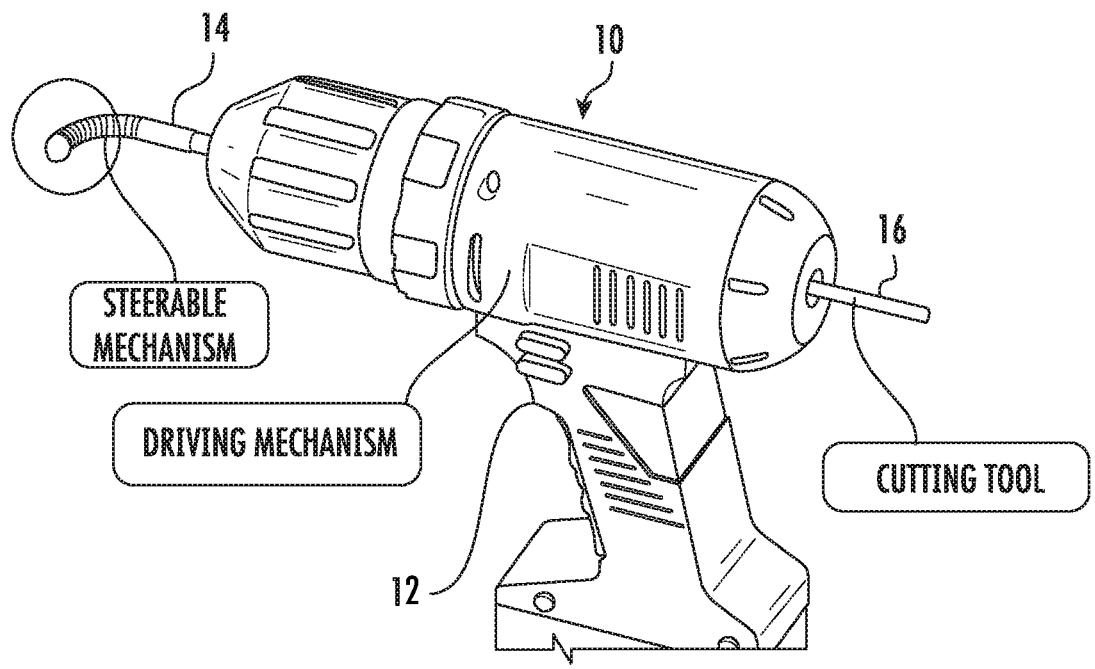
FIGS. 2A-2C illustrate perspective, side, and sectional views of a continuum dexterous manipulator (CDM), according to an embodiment of the present invention.
Figure 2B:
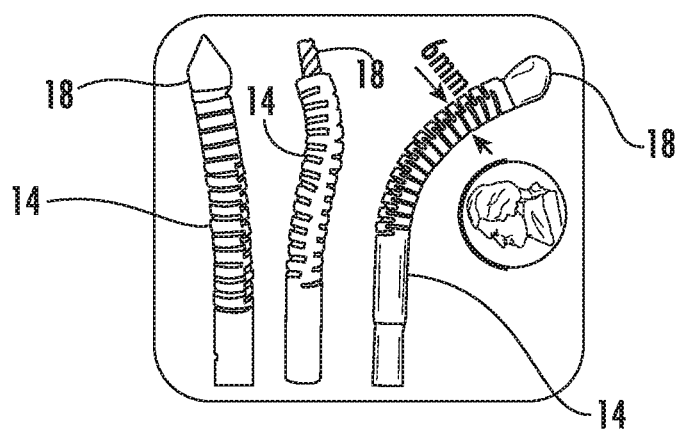
Figure 2C:
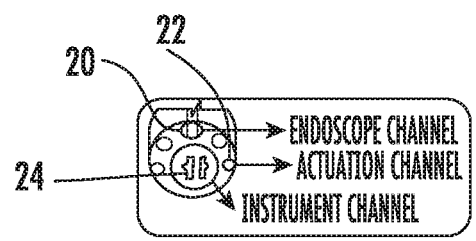

FIGS. 2A-2C illustrate perspective, side, and sectional views of a CDM, according to an embodiment of the present invention. FIG. 2A illustrates a steerable device, according to an embodiment of the present invention. The steerable device 10 includes a driving mechanism 12, a steerable mechanism 14, and a cutting tool 16. The driving mechanism 12 can be configured to provide rotation to the steerable mechanism 14 for drilling and also curvature and movement of the steerable mechanism 14. The cutting tool 16 can be a separate component from the steerable mechanism 14. The cutting tool 16 is inserted through a channel in the driving mechanism 12 and steerable mechanism 14. As illustrated in FIG. 2B the cutting tool 16 can include different drill bits 18 of the cutting tool 16 at the distal end of the steerable mechanism 14. FIG. 2C illustrates a sectional view of the steerable mechanism 14. The steerable mechanism 14 defines a number of channels, including, but not limited to, an endoscope channel 20, an actuation channel 22, and an instrument channel 24.

Further with respect to FIGS. 2A-2C, the driving mechanism 12 includes the main body of the handheld device and contains the motors and battery of the system. It has buttons for turning the device on or off, controlling the bending angle of the steerable mechanism, and speed of the cutting tool. The button for control can take the form of a joystick or directional buttons. Further, in some embodiments the steerable device can be actuated by robotic control or computerized control. In such an embodiment, the steerable device can be controlled with a console, a computing device, a tablet, or any other suitable means for control known to or conceivable to one of skill in the art. The steerable mechanism 14 is a flexible envelope which can be a continuum robot, a multi-backbone continuum robot, or a jointed robot with small size links, or any flexible device with a controllable bending angle. The bending angle of this mechanism can be controlled by pulling or otherwise engaging its embedded cables. Considering the application, the CDM of the present invention can be made of a metal like titanium or nitinol alloy or can be 3D-printed using nonmetal materials. The design of this flexible envelope (length, diameter, and shape of the notches) can be changed based on the application. Also, an endoscope can be embedded in one of the channels of the steerable mechanism as shown in FIG. 2C. The flexible cutting tool 16 is passed through the driving mechanism and tool channel of the steerable mechanism. Based upon the application, it can be inserted from proximal or distal end of the device. The device 10 has a quick connection mechanism to facilitate installation of the tool before, after or during bending of the bending motion of the steerable mechanism 14. Further, it can be coupled to an irrigation and aspiration mechanism to help debriding and cutting procedure. A button can be considered to control aspiration and irrigation during cutting procedure.

Figure 3A:
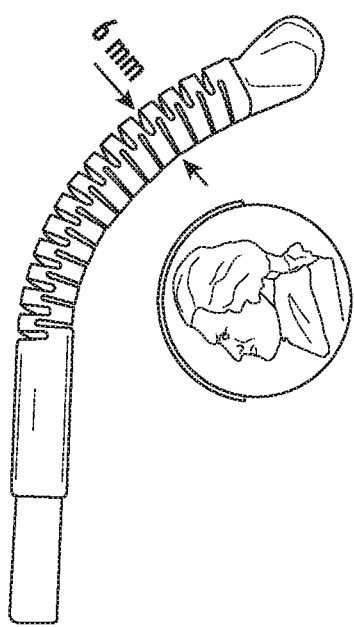
FIGS. 3A and 3B illustrate a CDM and cutting tools, according to an embodiment of the present invention.
Figure 3B:
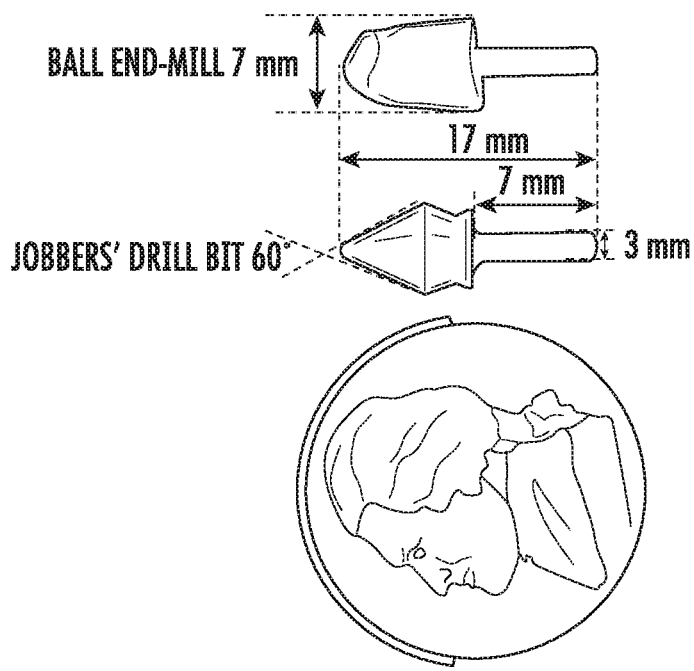

FIGS. 3A and 3B illustrate a CDM and cutting tools, according to an embodiment of the present invention. As illustrated in FIG. 3A, the CDM is fabricated from two nested nitinol tubes with a 35 mm length, an outer diameter of 6 mm and inner tool channel diameter of 4 mm (not pictured). Post-machining, via a wire EDM process, notches are cut along the length of the CDM that constrain bending to a single plane while providing out-of-plane stiffness. In addition, cables passing through the walls of the CDM perform pull-pull actuation of the manipulator into either C or S shapes. FIG. 3B illustrates a pair of cutting tools. One cutting tool takes the form of a ball end-mill and the second takes the form of a jobbers' drill bit. In FIG. 3A, the ball end-mill drill bit is engaged with the CDM. Based on the type of surgery (i.e. osteonecrosis or bone fracture), various types of cutting tools can be utilized along with the embedded endoscope.

Figure 4:
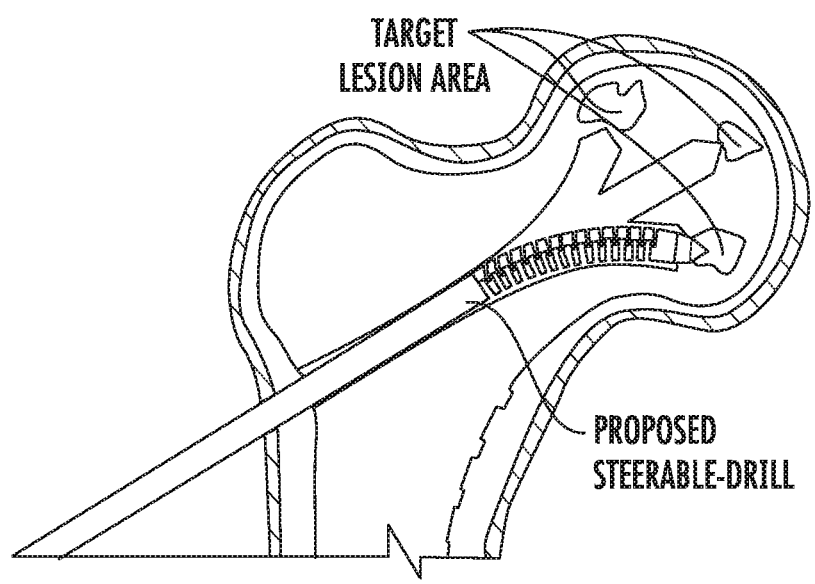
FIG. 4 illustrates a steerable device used to target lesion areas in bone, according to an embodiment of the present invention.

FIG. 4 illustrates a steerable device used to target lesion areas in bone, according to an embodiment of the present invention. As illustrated in FIG. 4, the steerable device can be actuated to target the lesion areas. The cutting end is engaged to excavate the bone from the lesion areas. While the steerable device is being shown herein with respect to targeting lesions and osteonecrosis in a femur, the steerable device can be used in any application known to or conceivable to one of skill in the art.

Cutting tool geometry has a major influence in bone cutting behavior. For instance, drill diameter, cutting face, number of flutes, helix angle, and the drill point angle directly affect cutting behavior during bone drilling. Of note, the optimal geometry features are defined by the cutting direction and bone material properties. On the other hand, the fabricated cutting tool needs to be able to meet all other design criteria assigned by the CDM. Therefore, the following design criteria were considered for the proposed cutting tool.

Geometry of the cutter: In conventional straight bone drilling, drilling occurs along the axis of the drill bit; however, in curved drilling, it is a combination of cutting using the edge (side) and tip of the drill bit. The aforementioned tool geometry features need to be optimally characterized for this cutting task.

Buckling and stiffness trade off: In common drilling tasks, due to rigidity of the drilling tool 1) buckling of the drill bit is less likely to happen, and 2) the feeding force is transferred directly to the tip of the cutter. However, a system including a flexible cutter in a flexible continuum robot is vulnerable to buckling and inadequate contact force during drilling procedure.

Tool dimension: This parameter is dependent on the CDM outer diameter (6 mm), its tool channel diameter (4 mm), and permissible drill holes depending on the type of medical procedure and the anatomy of the patient (for instance, in the core decompression procedure—defined by the femur neck geometry (usually less than 12 mm)).

Considering all of these requirements, two tools with different geometries are included in the present invention: a classic surgical drill bit and a ball-end mill. These two drill bit geometries are illustrated in FIG. 3B. The present invention necessitates a type of cutting tool that can be used for both side-cutting and penetration. Each fabricated tool includes of 4 parts: a rigid stainless steel tube (2.8 mm OD), a 3.25 mm flexible torque coil (Asahi Intecc USA, Inc.) with 35 mm length, an oil-less bush (OD=6.5 mm, ID=4.5 mm), and a cutter with a shaft diameter of 7 mm. Diameters of the torque coil and the rigid tube were chosen to be easily inserted through the CDM tool channel. To minimize buckling and avoid making big holes in the femur, the outer diameter of the cutting tool is considered to be larger than the outer diameter of the CDM while less than 12 mm. This ensures that the external cutting forces are transferred directly to the body of the CDM. Due to the CDM geometry, it avoids buckling and bending of the robot in an unwanted plane. Further, the considered oil-less bush reduces the friction between the cutter and the CDM tip during rotation. For the cutters, a 7 mm ball-end carbide end mill with two flutes and helix angle of 30° (8878A18, McMaster-Carr) is used, and a high-speed steel Jobbers drill bit with a sharp 60° point angle (27465A419, McMaster-Carr). The drill bit shaft is cut to 7 mm length (for a total drill length of 17 mm), and the shaft diameter turned down to 3.0 mm to insert into the torque coil, as illustrated in FIG. 3B. Preliminary experiments showed that the Jobbers' drill bit is not the best candidate for the curved-drilling guided by the CDM due to its limited capability in side cutting. Therefore, experiments to demonstrate the present invention are limited to a ball-end mill cutter. The end mill cutter geometry enabled the drill bit to cut into the material along its axis as well as during bending motion of the CDM.

Aside from drill geometry, bone drilling parameters such as rotational speed of the drill and feeding speed/force of the drill affect the performance of the conventional bone cutting system. To check the feasibility of using curved-drilling by the CDM in the core decompression procedure, the effect of these parameters on the cutting performance of the system are examined. Additionally, due to the nature of the curved-drilling, resultant tip velocity of the integrated system comprises feeding velocity of the drill and sweeping velocity of the CDM, which adds another drilling parameter to drilling performance. Sweeping velocity of the CDM in free bending is defined by tensioning (pulling) the actuation cables and is variable during bending motion of the CDM. In particular, faster changes in the pulling force cause faster changes in the velocity of the tip.

Drilling trajectory is another important parameter in drilling by a continuum robot. This is dependent on various parameters such as material properties and homogeneity, contact forces during drilling, buckling, etc. Constant pulling tension results in a unique shape for the integrated CDM and the flexible tool in free-bending motion. However, the configuration of the integrated cutting system during drilling and its repeatability for a constant pulling tension is an unknown parameter and needs to be experimentally identified. To evaluate drilling performance and trajectory of the present invention, rotational velocity of the cutter, feed-velocity of the sample, and the pulling tension of the CDM are considered. The optimal combination of these controllable input parameters is also evaluated, which helps to plan an effective drilling trajectory for reaching the target necrotic lesions.

Figure 5A:
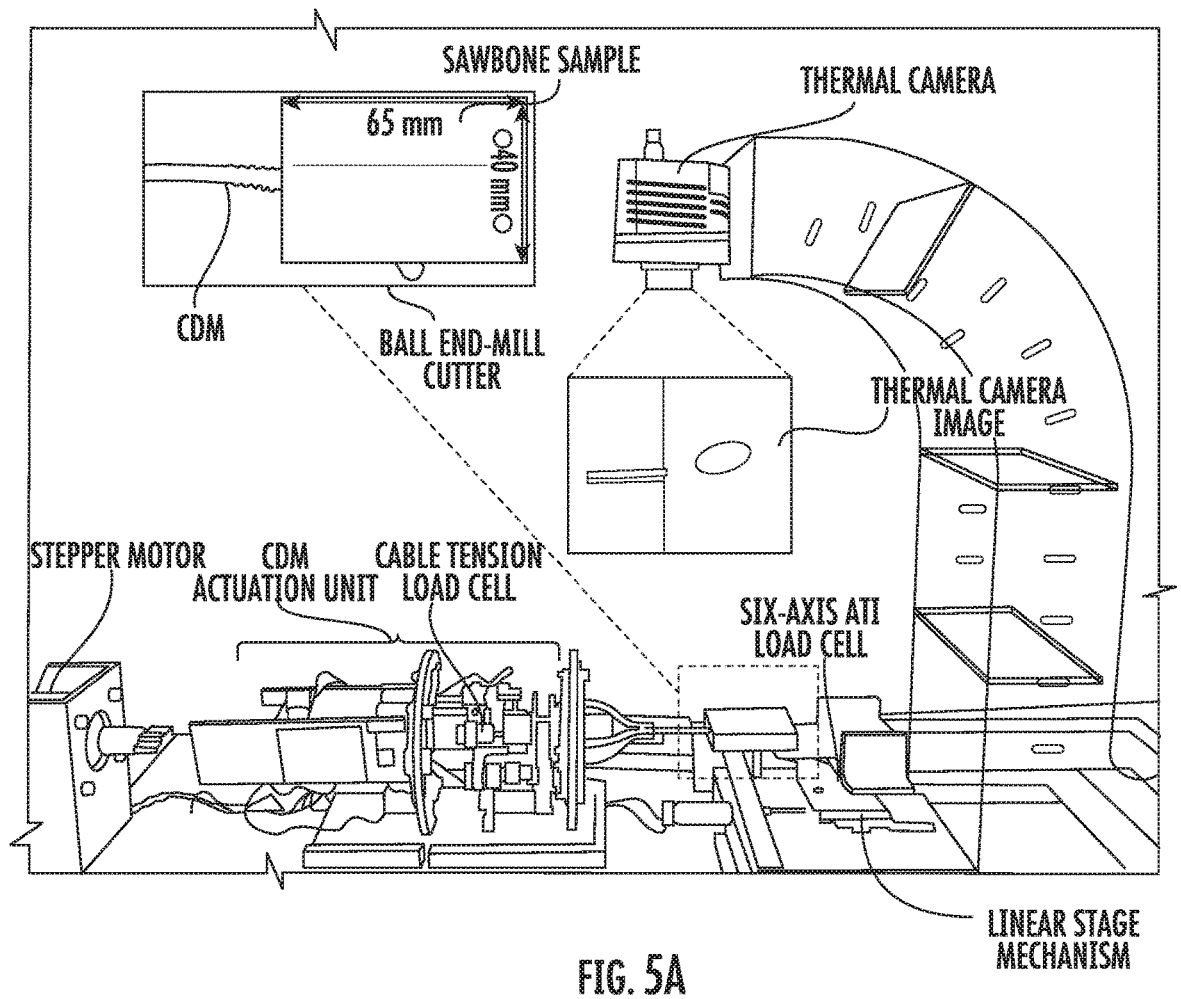
FIGS. 5A and 5B illustrate perspective views of an experimental setup to test an embodiment of the steerable device according to the present invention.
Figure 5B:
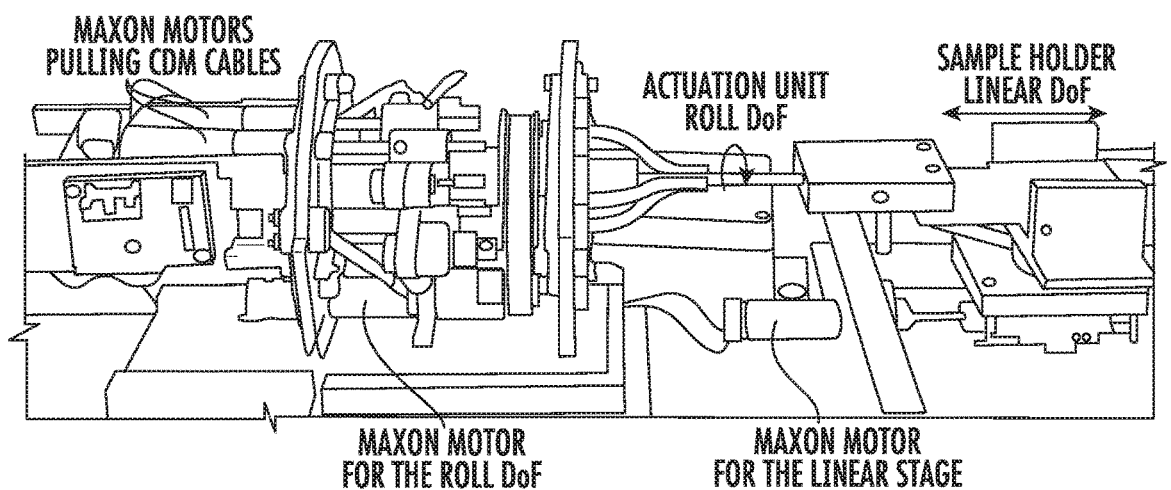

FIGS. 5A and 5B illustrate perspective views of an experimental setup to test an embodiment of the steerable device according to the present invention. FIG. 5A illustrates the setup for the curved-drilling experiments, and FIG. 5B illustrates the actuation unit and sample holder DoFs. To eliminate the variability encountered when testing with human cadaver bone, this exemplary experiment simulates the cancellous bone using Sawbones biomechanical bone model material (block 15 PCF, Pacific Research Laboratories, USA) because it offer uniform and consistent physical properties. For the experiments, rectangular samples (65 mm×40 mm×9 mm) were made from this Sawbones block, as illustrated in FIGS. 5A and 5B.

The developed curved-drilling experimental setup is capable of evaluating drilling performance of the system during bending and feeding motions, as illustrated in FIGS. 5A and 5B. This setup includes three main modules: a two degrees of freedom sample holder mechanism, CDM actuation unit module, and tool actuation module. The CDM actuation unit has 4 DC motors (RE16, Maxon Motor Inc.) with spindle drives (GP16, Maxon Motor, Inc.) to pull the CDM cables and provide S-bend capability to the CDM. In addition, the actuation unit is rotated about its central axis (roll DoF) by another DC motor (RE16, GP16C, Maxon Motor Inc.). The CDM can have planar bend and can rotate about its central axis (using the 360 degree roll motion) to change the bending plane, as illustrated in FIG. 5B. Furthermore, the setup has one stepper motor (DMX-UMD-23, Arcus Technology, Inc.) which rotates the cutting tool and a brushless DC motor (RE16, Maxon Motor, Inc.) with a spindle drive (GP16, Maxon Motor, Inc.) that moves a cart carrying the sample on a linear stage to provide the sample feeding motion. This mechanism is mounted in front of the tip of the tool. The stepper motor was chosen to ensure sufficient torque for cutting during the experiments.

The actuation unit also has four load cells (Model 31Mid, Honeywell Inc.) to read cable tensions, and provides a central channel for passing the tools through the CDM. Further, to better interpret the drilling behavior, interaction forces between the sample and the cutter during drilling were measured by a six-axis force/torque sensor (Mini 40, ATI Industrial Automation, Inc.) installed under the cart carrying the sample. A custom C++ interface performed independent velocity or position control of each motor using libraries provided by Maxon and communicated over a single mini-USB cable. In addition, an overhead thermal camera (Gobi, Xenics nv, Leuven, Belgium) tracked the cutting tool through the sample.

There is no clear indication about the optimum speed for conventional bone drilling. A speed range between 400-10000 rpm is preferred. Several preliminary experiments with various speeds were conducted with a device according to an embodiment of the present invention and the best performance (in terms of removing material, not buckling, proceeding inside material, etc.) can be achieved at 2250 rpm, which was the maximum allowable speed of the used stepper motor. This value is within the accepted drilling velocity range. Also, similar to rotational speed, various feed-rate values are also possible. A set of preliminary experiments were performed and 0.05, 0.10, and 0.15 mm/s were found to be an appropriate range, considering the aforementioned criteria, for the system of the present invention. The experiments focused on evaluating the system for three sample feed-velocities (0.05, 0.10, and 0.15 mm/s) and four pulling tensions (6, 10, 15, and 25 N).

In each experiment, one constant pulling tension was set and the feed-velocity was varied to completely insert the CDM inside the sample and investigate how it affects tool performance. Each experiment was repeated three times, for a total of 36 experiments. Before starting each experiment, the sample with a high precision balance (1601, Sartorius Inc.) and adjusted its position in the cart with respect to the drill. Then, the drill was initially inserted into the sample at a depth of 5 mm before beginning the experiment. Simultaneous tension control and sample feed-velocity control were performed in each experiment and the cutting trajectory was recorded by the thermal camera. Furthermore, cable tension and the cutting forces were recorded during the experiments. Upon completion, the sample was weighed to calculate the removed weight. Of note, in these experiments the focus was on the planar drilling trajectories due to limitations imposed by the bending motion of the CDM. However, considering the current core decompression procedure, using a planar trajectory, surgeons are able to access the lesion area. In addition, considering the roll motion of the actuation unit, the proposed system of the present invention is capable of changing the plane of drilling. To control the cable tension during the experiments, the plane of bend was set, the roll DoF of the actuation unit locked and the following control paradigm used:

$$V = k \cdot (T - T_{des})$$

where V is the commanded motor velocity, T is the measured cable tension by the load cell, $T_{des}$ is the desired cable tension, and k is a proportional constant. Based on $T_{des}$, an appropriate k was chosen to ensure an equal rising time response in each experiment.

Figure 6A:
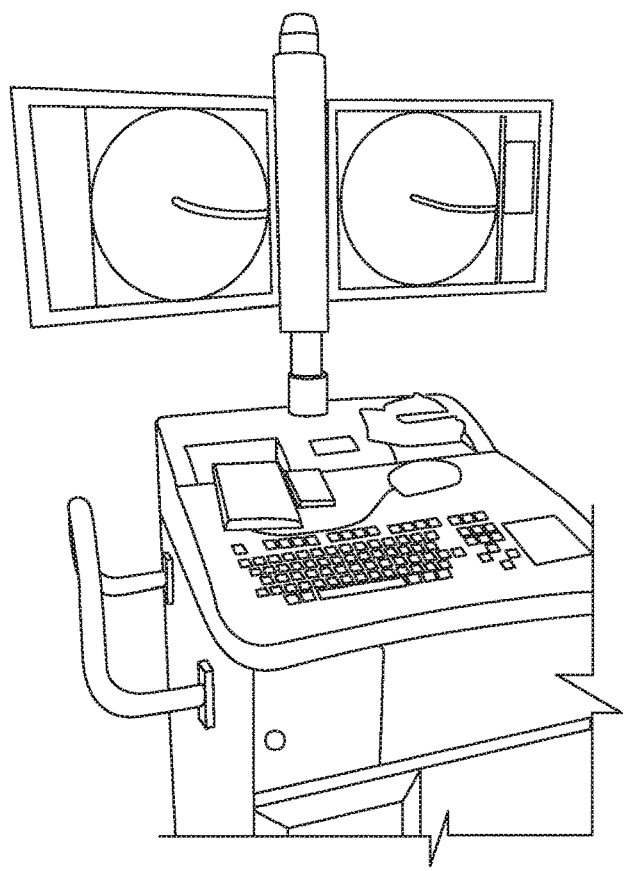
FIG. 6A illustrates a perspective view of using C-arm to take an X-ray image of the integrated drilling system inside the sample.
Figure 6B:
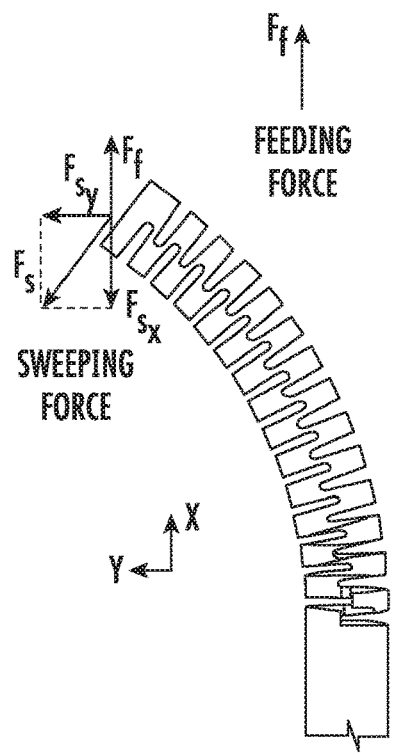
FIG. 6B illustrates a side-view of a simplified free-body diagram of a Sawbone sample during curved-drilling.

Two types of results were investigated based on the collected data for each combination of cable tension and feed-velocity: drilling trajectory and drilling behavior. To investigate the dependency of the drilling trajectory to the drilling parameters, the shape of the CDM inside the drilling tunnel was reconstructed after the experiments. A C-arm (ARCADIS Orbic, Seiemens; Munich, Germany) was used to take an X-ray image of the integrated drilling system inside the sample, as illustrated in FIG. 6A. FIG. 6A illustrates a perspective view of using C-arm to take an X-ray image of the integrated drilling system inside the sample, and FIG. 6B illustrates a side-view of a simplified free-body diagram of a Sawbone sample during curved-drilling.

Figure 7:
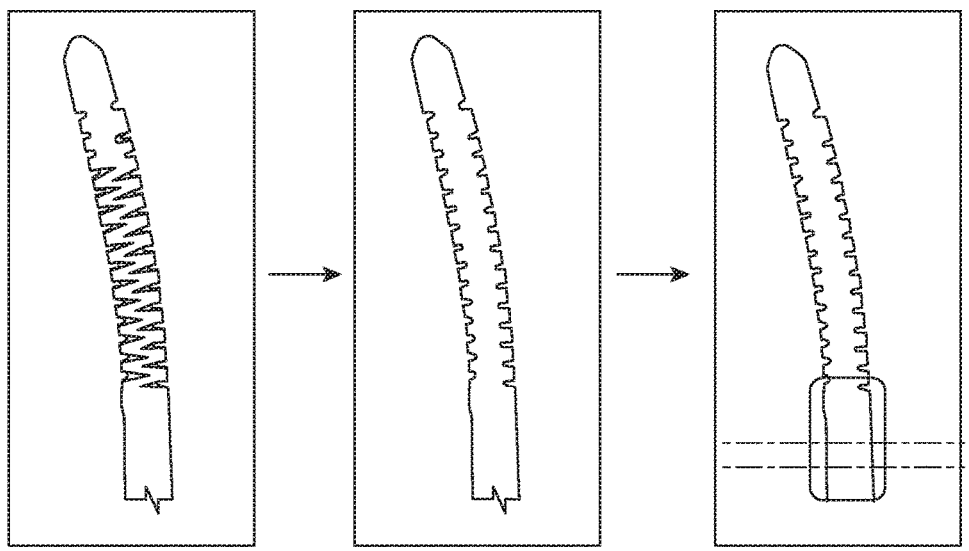
FIG. 7 illustrates 2D-3D registration steps for the reconstruction of the CDM shape from an X-ray Image.
Figure 7:
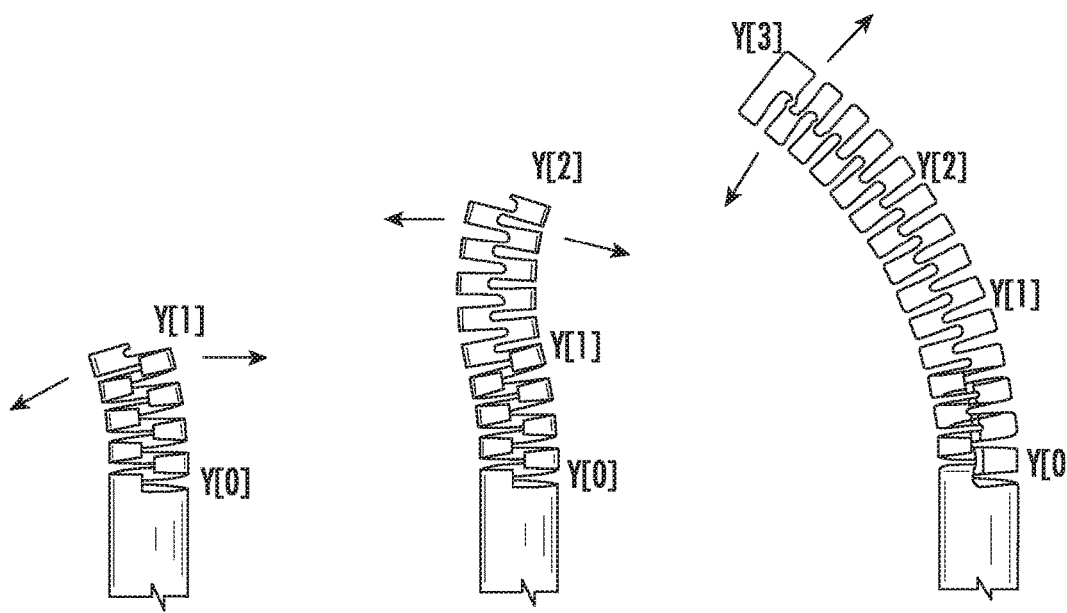

A 2D-3D registration method was developed to register the CDM shape from the X-ray Images. In this method, the input X-ray image is first converted to a black-and-gray image and then the position of the CDM base is determined, as illustrated in FIG. 7. The CDM kinematics can be effectively modeled as a series of 27 co-axial pin joints along the long axis of the manipulator. FIG. 7 illustrates 2D-3D registration steps for the reconstruction of the CDM shape from an X-ray Image.

During registration, a 4-point cubic spline interpolates these 27 joint angles. Based on these 4 knot points, the CDM can be broken into three distinct segments and be registered sequentially. The registration process simulates a digital image and compares the simulated image to the X-ray image using an edge distance similarity measure. Based on the simulations performed, the average joint degree error was about 0.2 degrees.

Figure 8:
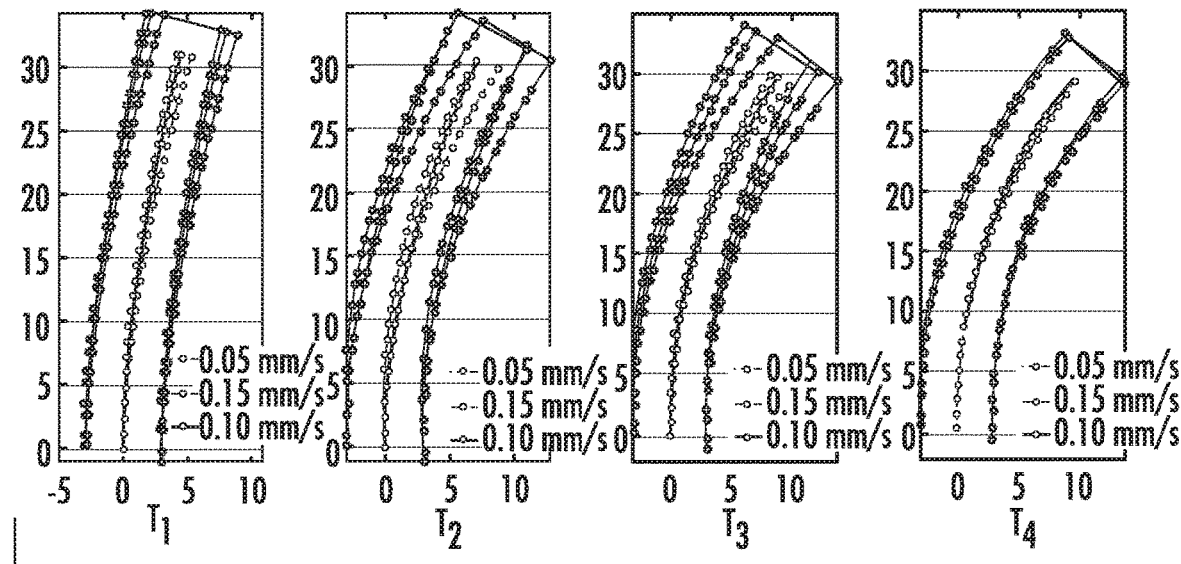
FIG. 8 illustrates graphical views of drilling trajectories for each combination of fixed pulling tensions (6, 10, 15 and 25 N) and various feed-velocities (0.05, 0.10 and 0.15 mm/s).
Figure 9:
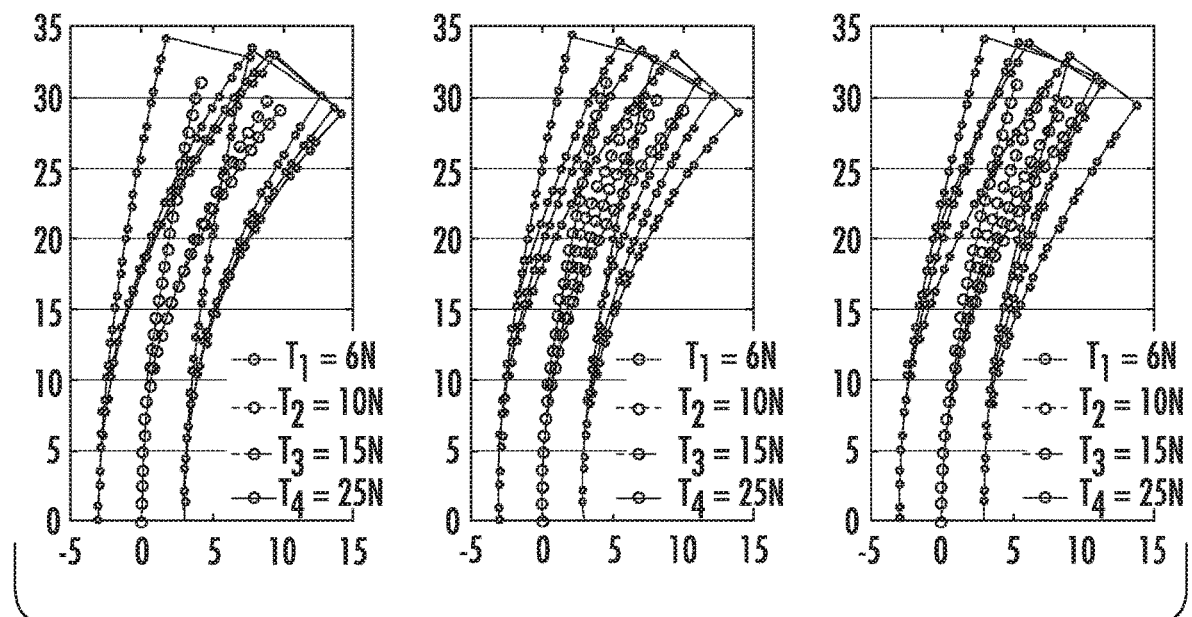
FIG. 9 illustrates graphical views of drilling trajectories for a constant feed-velocity (0.10 mm/s) and various pulling tensions (6, 10, 15 and 25 N).
Figure 10:
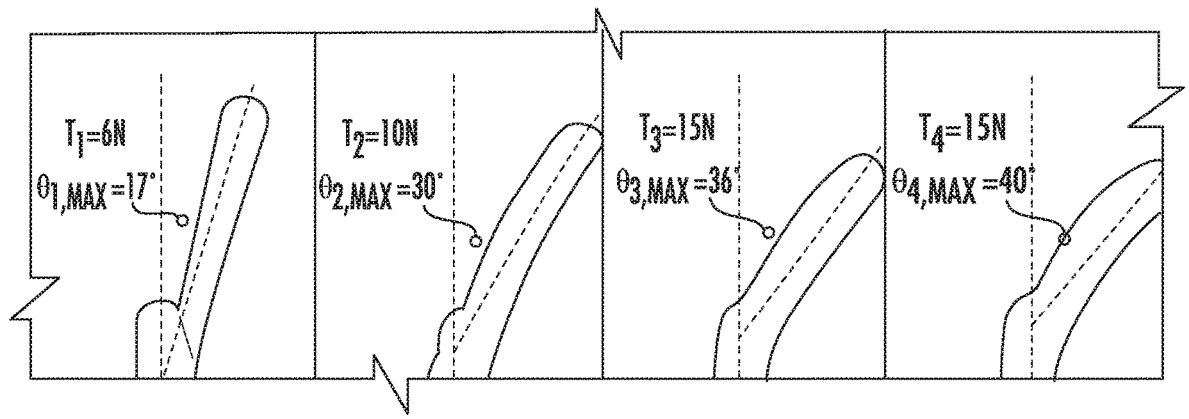
FIG. 10 illustrates cross-sectional views of the drilled samples in the case of 0.10 mm/s feed-velocity and various pulling tensions (6, 10, 15 and 25 N) with the corresponding maximum bend angle.

FIG. 8 illustrates graphical views of drilling trajectories for each combination of fixed pulling tensions (6, 10, 15 and 25 N) and various feed-velocities (0.05, 0.10 and 0.15 mm/s). FIG. 8 demonstrates the results of the drilling trajectories for each combination of fixed tensions (6, 10, 15 and 25 N) and various feed-velocities (0.05, 0.10 and 0.15 mm/s). The centerline of the drilled tunnel as well as the border of the CDM has been shown to better demonstrate the generated curved tunnel. Inspection of these plots shows that almost all feed-velocities for constant pulling tension make identical curves. Maximum calculated bending deviation from the averaged centerline is about 3 degrees. FIG. 9 illustrates graphical views of drilling trajectories for a constant feed-velocity (0.10 mm/s) and various pulling tensions (6, 10, 15 and 25 N). FIG. 9 represents the trajectory of the drill for a constant feed-velocity and various tensions. As shown, larger tensions result in larger bend angles for a constant feed-velocity. Also, these figures show the repeatability of the drilling behavior for each combination of the drilling parameters. FIG. 10 illustrates cross-sectional views of the drilled samples in the case of 0.10 mm/s feed-velocity and various pulling tensions (6, 10, 15 and 25 N) with the corresponding maximum bend angle. The maximum bend angle is the angle between the initial insertion orientation (yellow line) and the tangent line to the end of the curved tunnel (red line). The minimum bend angle—nearly 17 degrees—occurs with 6 N cable tension and 0.10 mm/s feed-velocity. The maximum bend angle of 40 degrees occurs with 25 N cable tension and 0.10 mm/s feed-velocity, which is two times greater than the maximum reported bending angle.

Figure 11:
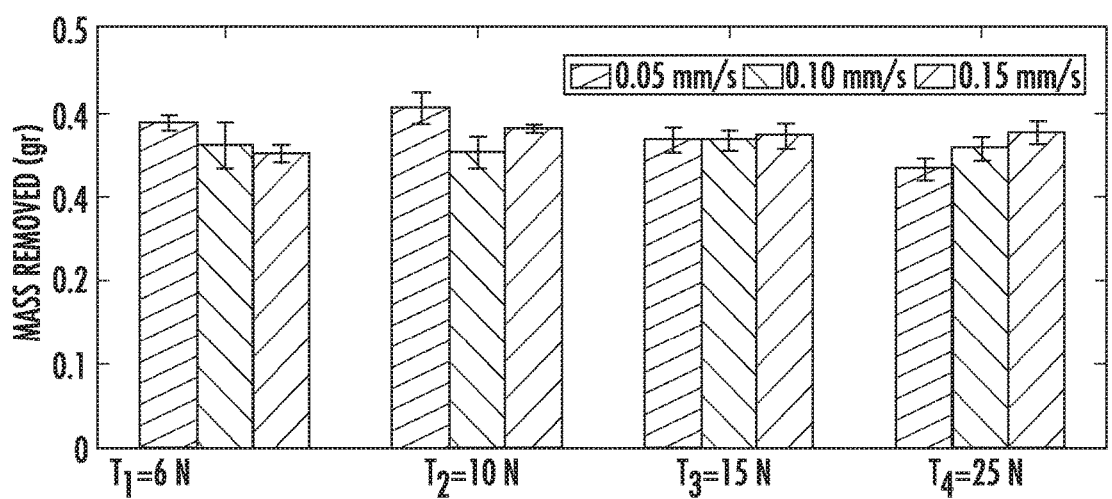
FIG. 11 illustrates a graphical view of mass removal results for each combination of fixed pulling tensions (6, 10, 15 and 25 N) and feed-velocities (0.05, 0.10 and 0.15 mm/s).
Figure 12:
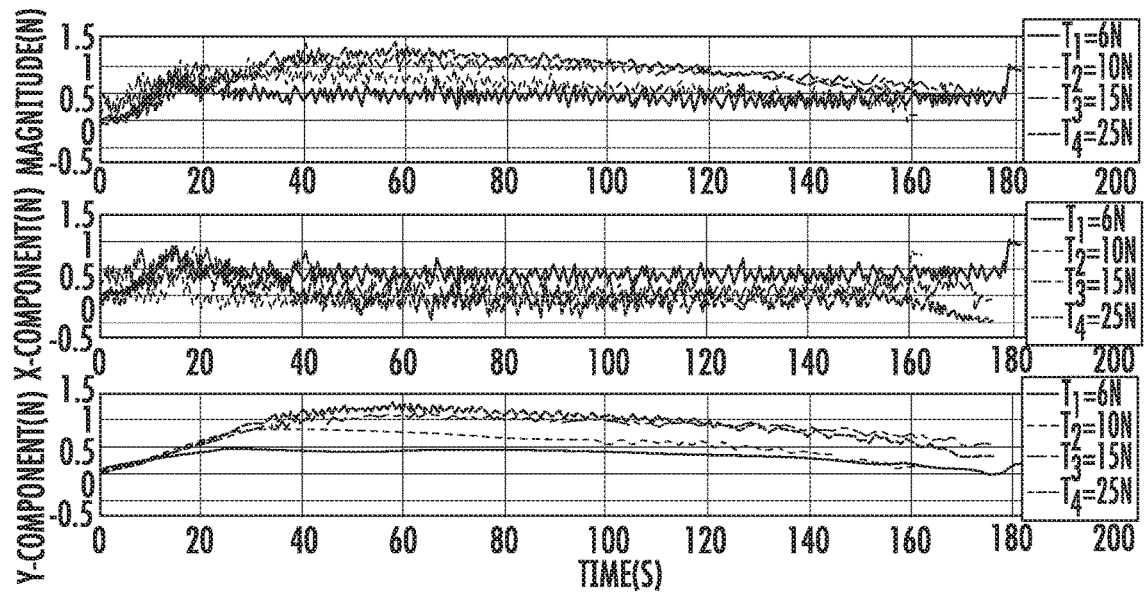
FIG. 12 illustrates graphical views of magnitude and components of $F_R$ for the cases of constant feed-velocity (0.15 mm/s) and various pulling tensions (6, 10, 15 and 25 N).
Figure 13:
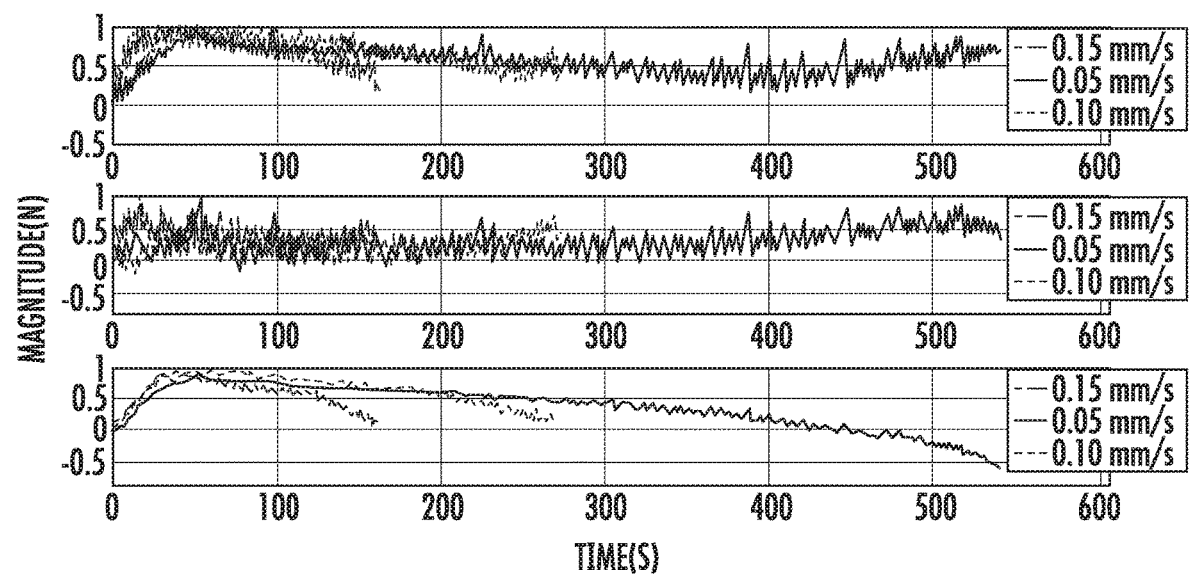
FIG. 13 illustrates graphical views of magnitude and components of $F_R$ for each combination of fixed pulling tensions (10 N) and various feed-velocities (0.05, 0.10 and 0.15 mm/s).

The mass removal amount (about 0.4 g) does not significantly change with varying feed-velocity and pulling tension, as illustrated in FIG. 11. Calculated trajectories, illustrated in FIG. 9 indicate the same insertion length of the CDM in the samples. The behavior observed in FIG. 11, therefore, is justified given the homogeneity of the samples. FIG. 11 illustrates a graphical view of mass removal results for each combination of fixed pulling tensions (6, 10, 15 and 25 N) and feed-velocities (0.05, 0.10 and 0.15 mm/s). FIG. 6 demonstrates the simplified free-body diagram of a sample during curved-drilling. The force generated by the sweeping motion of the CDM ($F_s$) is normal to the cutting trajectory while the force caused by the feeding motion of the sample ($F_f$) is in X direction. The resultant drilling force ($F_R$) is the vector summation of these two forces. The Y component of $F_R$ is only due to the CDM motion ($F_{R_y}=F_{s_y}$) while its X component is due to the opposing X components of feeding and sweeping motions ($F_{R_x}=F_f-F_{s_x}$). It is notable that the cutting forces and moments are more complex than the presented model; however, the measured forces in FIGS. 12 and 13 are justified using this simplified model. FIG. 12 illustrates graphical views of magnitude and components of $F_R$ for the cases of constant feed-velocity (0.15 mm/s) and various pulling tensions (6, 10, 15 and 25 N). FIG. 13 illustrates graphical views of magnitude and components of $F_R$ for each combination of fixed pulling tensions (10 N) and various feed-velocities (0.05, 0.10 and 0.15 mm/s).

FIG. 12 represents the effect of increasing cable tension on the magnitude and components of $F_R$ for the case of 0.15 mm/s feed-velocity (fixed $F_f$). As shown: 1) a larger cable tension results in a higher $F_R$ while the overall trend of the drilling force is similar for all cable tensions. 2) The overall trend of $F_R$ is generally determined by its Y component rather than the X component. It is notable that for the smallest pulling tension (6 N) both the X and Y components contribute equally. In this case, contribution of the feeding force in $F_R$ is greater than the components of CDM motion. Increasing the pulling tension magnifies $F_s$ and results in larger $F_{sy}$ and smaller $F_{sx}$.

FIG. 13 demonstrates the magnitude and components of $F_R$ for the cases of constant 10 N pulling tension and three feed-velocities. A similar trend is observed after time scaling for all of the curves. A constant pulling tension provides constant $F_s$ for all feed-velocities, therefore, a similar $F_{Ry}$ pattern is expected in all cases, as illustrated in FIG. 13. The initial rising part in FIGS. 12 and 13 is the required time for the controller to reach the desired tension. Comparing X and Y components of $F_R$ indicates the reversed behavior of these forces. After the initial rise, the Y component decreases over time while the X component increases. This can be justified by the bending angle of the cutting tool tip—increasing bending angle causes a smaller $F_{sy}$ and a larger $F_{sx}$.

Sudden peaks in the X and Y force components were not observed in the experiments, as illustrated in FIGS. 12 and 13. This demonstrates that the designed steerable device can avoid buckling for the considered range of cable tensions and feed-velocities. Moreover, buckling reduces mass removal capability. The constant mass removal in these experiments, as illustrated in FIG. 11, further indicates that buckling did not happen in the conducted experiments.

The lesion in the femoral head may not be accessible using only one of the obtained drilling trajectories. A variable tension approach can be used during insertion of the CDM into the femur to generate different drilling trajectories. The dominant parameter in controlling the drill trajectory is the cable tension, while faster feed-velocities decrease cutting time. Considering this important result, a trajectory planning algorithm is used for four pulling tensions and constant feeding speed of 0.15 mm/s. The proposed method in this section may also be clinically applicable when the bone density of the patient is known from CT scans.

In this method, the desired trajectory is divided into a maximum of four segments where each segment is part (or all) of the obtained trajectories. In other words, the problem is to investigate whether suitable insertion lengths of each segment can be found that places the end-mill cutter tip at the target lesion location. Curves were fit to the obtained experimental trajectories. Given the arc length, the resultant end-point position (x, y) of each curve is calculated using the following equations:

$$s_i = \int_0^x \sqrt{1+(f_i'(x))^2}\, dx \quad i \in \{1, 2, 3, 4\} \quad y = f_i(x)$$

where $s_i$ is the known arc length, $f_i(x)$ is the fit curve corresponding to each cable tension ($T_i$), and $f'_i(x)$ is the derivative of the fit curve.

Figure 14:
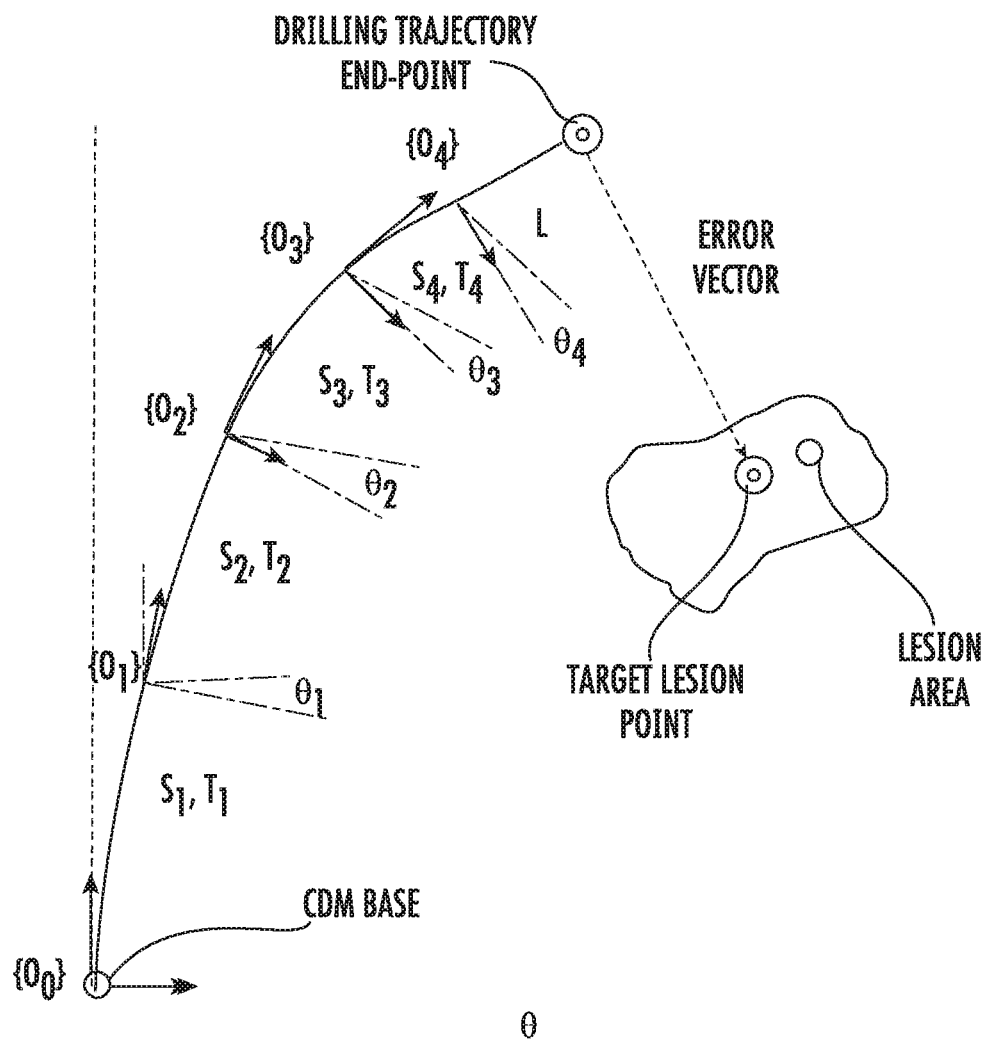
FIG. 14 illustrates schematic views of proposed preoperative trajectory planning using the obtained experimental results.

After finding the locations of the end-points (x, y) on each curve, these locations are related using the Denavit-Hartenberg method. Basically, the calculated end point of each curve has been defined in the local frame $\{O_j\}$, $j \in \{0, 1, 2, 3, 4\}$, therefore, these local frames are mapped to the global frame $\{O_0\}$, as illustrated in FIG. 14. FIG. 14 illustrates schematic views of proposed preoperative trajectory planning using the obtained experimental results. Here, the global frame $\{O_0\}$, is defined at the CDM base and each segment's end-point is the origin of the local frame $\{O_j\}$. The homogenous transformation matrix from $\{O_0\}$ to $\{O_4\}$ can be obtained as:

$$H_0^4 = H_0^1 \cdot H_1^2 \cdot H_2^3 \cdot H_3^4$$

$$H_i^j = \begin{bmatrix} \cos(\theta) & -\sin(\theta) & x_i \\ \sin(\theta) & \cos(\theta) & y_i \\ 0 & 0 & 1 \end{bmatrix}, \theta = \tan^{-1}(f_i'(x))$$

where $H_i^j$ is the homogeneous transformation matrix from frame j to i, and θ is the rotation angle between frames i and j.

Solving the following optimization problem gives feasible insertion arc lengths of each segment that result in error between drilling trajectory end-point and target lesion location:

$$\operatorname*{argmin}_{s_i} H_0^4 \cdot \begin{bmatrix} 0 \\ L \\ 1 \end{bmatrix} - \begin{bmatrix} x_d \\ y_d \\ 1 \end{bmatrix}_2 \text{ subject to } \left\{ \begin{array}{c} 0 < s_i \le 30 \text{ mm} \\ \sum_{i=1}^{4} s_i \le 35 \text{ mm} \end{array} \right\}$$

where L is the length of the end-mill cutter and $(x_d, y_d)$ is the location of the lesion in $\{O_0\}$. Trajectory planning is then sequential insertion of the CDM with the obtained length $s_i$ while applying the corresponding cable tension $T_i$.

Figures 15A, 15B, 15C:
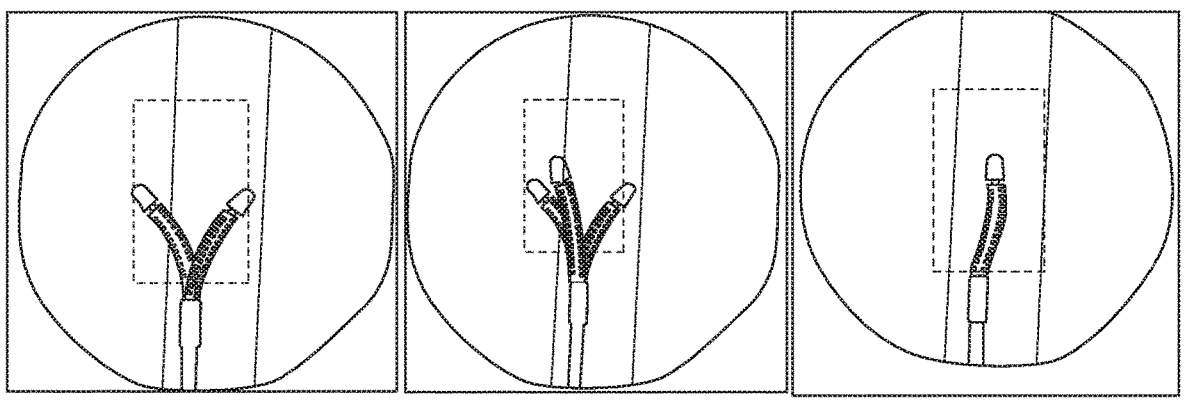
FIG. 15A illustrates a two-branch drilling tunnel made in two steps by two similar cutting parameters (25 N, 0.15 mm/s)
FIG. 15B illustrates a three-branch drilling tunnel made in three steps by two similar cutting parameters (25 N, 0.15 mm/s) followed by a combination of 10 N pulling tension and 0.15 mm/s feed-velocity (middle tunnel)
FIG. 15C illustrates an S-shape drilled tunnel made by two similar cutting parameters (25 N and 0.15 mm/s).

In treatment of necrotic lesions, minimizing the damage of the healthy bone tissue and decreasing the weakening of the femoral neck is very crucial. In this regard, considering the presented results, the feasibility of using the proposed system is examined in creating multiple connected branches and S-shape tunnels. FIGS. 15A-15C demonstrate the X-ray images of a two- and three-branch tunnel and an S-shape drilled tunnel. FIGS. 15A-15C illustrate image views of a steerable device according to an embodiment of the present invention. FIG. 15A illustrates a two-branch drilling tunnel made in two steps by two similar cutting parameters (25 N, 0.15 mm/s); FIG. 15B illustrates a three-branch drilling tunnel made in three steps by two similar cutting parameters (25 N, 0.15 mm/s) followed by a combination of 10 N pulling tension and 0.15 mm/s feed-velocity (middle tunnel); and FIG. 15C illustrates an S-shape drilled tunnel made by two similar cutting parameters (25 N and 0.15 mm/s).

Figure 1:
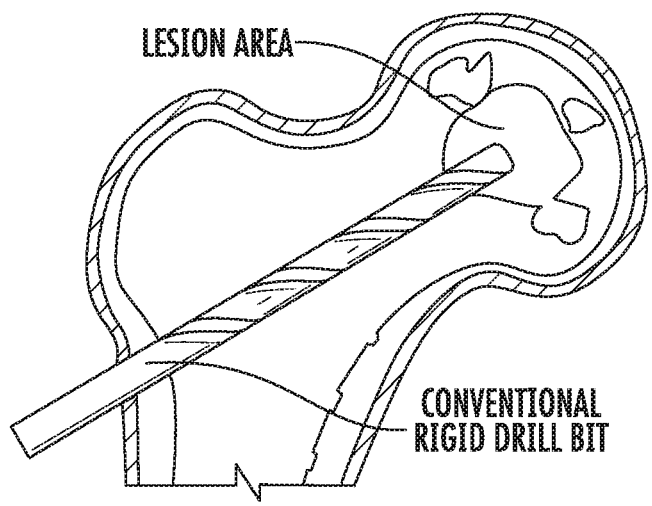
FIG. 1 illustrates a side view of a prior art drill solution.
Figure 16A:
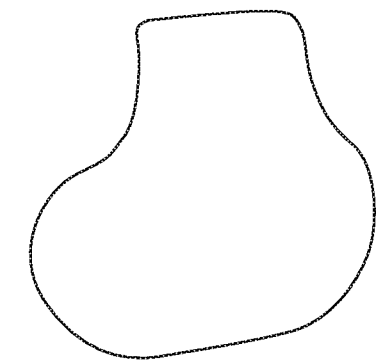
FIG. 16A illustrates curved drilling experiments on human femur medial epicondyle.
Figure 16B:
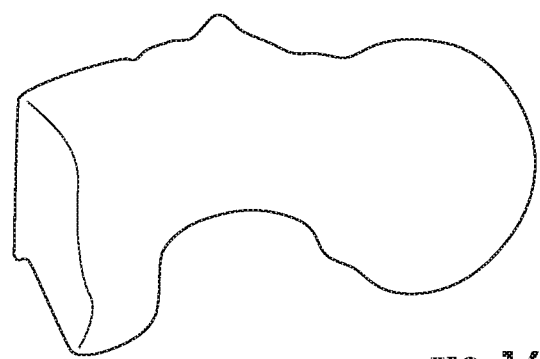
FIG. 16B illustrates curved drilling on neck specimens.
Figure 16C:
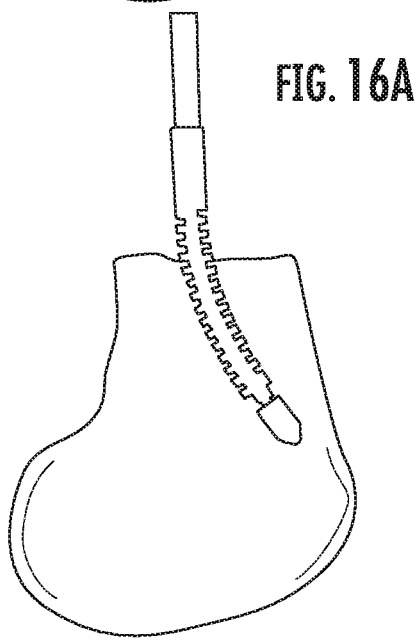
FIGS. 16C and 16D are their respective X-ray images after curved-drilling: combinations of 15 N pulling tension and 0.10 mm/s feed-velocity in FIG. 16C, and 25 N pulling tension and 0.10 mm/s feed-velocity in FIG. 16D are shown.
Figure 16D:
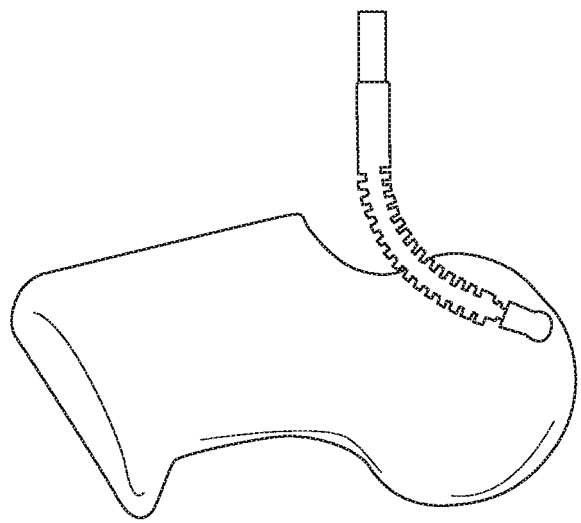

The three-branch sample, for instance, simulates three various locations of the lesions which can be reached with minimum damage to the healthy bone compared to the conventional core decompression approach using rigid tools, as illustrated in FIG. 1. Moreover, an S-shape drilling capability can increase the ability for drilling selective trajectories with the least excursion. This allows for the most effective removal of the necrotic area with the least damage to normal bone. The technical feasibility of using the proposed steerable device on human cadaveric specimens was also validated, as illustrated in FIGS. 16A-16D. FIGS. 16A-16D illustrate image views of curved drilling experiments, according to an embodiment of the present invention. FIG. 16A illustrates curved drilling experiments on human femur medial epicondyle, and FIG. 16B illustrates curved drilling on neck specimens. FIGS. 16C and 16D are their respective X-ray images after curved-drilling: combinations of 15 N pulling tension and 0.10 mm/s feed-velocity in FIG. 16C, and 25 N pulling tension and 0.10 mm/s feed-velocity in FIG. 16D are shown.

The medial epicondyle and neck of femur specimens were used and preliminary experiments were performed. These preliminary results support feasibility of using the proposed drilling approach in treatment of osteonecrosis.

The key parameter in controlling the drill trajectory is the cable tension, while faster feed-velocities decrease cutting time. Using these parameters and the obtained cutting trajectories, a preoperative trajectory planning has been proposed. In addition, feasibility of the presented system in S-shape and multi-branch drilling was successfully verified. Further, the viability of the proposed curved-drilling concept using the introduced steerable device was successfully demonstrated on human cadaveric bone. Although, herein, the behavior of the presented curved-drilling system is presented for the core decompression application, the results are also applicable to other types of surgeries (e.g. ACL reconstruction).

According to another embodiment of the present invention, a novel handheld device with various interchangeable cutting tools is paired with the continuum manipulator based on the cutting task. For instance, for the drilling applications a flexible drill bit and for the surface cutting an appropriate flexible milling tool can be inserted in the tool channel of a steerable device. The user can control the bending angle of the steerable cutting device to guide the cutting tool to the desired path as well as the rotational speed of the cutting tool. The designed flexible tools of this handheld tool can be attached to a vacuum pump and water source for simultaneous irrigation and aspiration during the cutting procedure. These features are inevitable for medical applications. The user can change the cutting tool before, after or during the bending motion of the steerable part. Also, an endoscope can be embedded in the surface body or can pass through tool channel of the of the steerable mechanism of the device to help user for better navigation.

Also, more technically, another novelty of this device lies in the ability to create a C-shape or S-shape curved path. Using a continuum manipulator as the steerable part of this cutting device has two advantages; first it guides the cutter through a highly-curved path and second it avoids buckling of the flexible cutter while reducing vibrations during cutting procedure. Examples of the use of this handheld steerable cutting device for medical applications can be in orthopedic surgeries (e.g. ACL reconstruction, treatment of Osteonecrosis, treatment of Osteolysis) or spine surgeries for reaching inaccessible regions to treat tumors.

Figure 17:
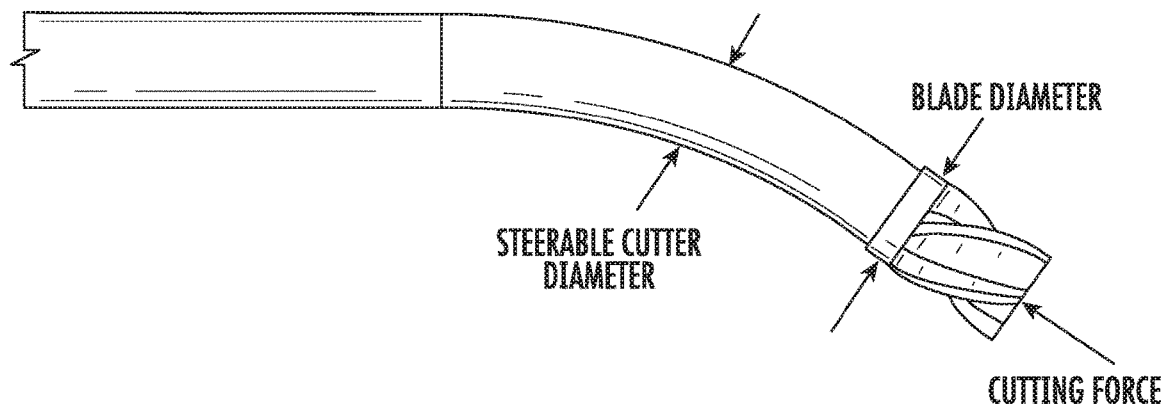
FIG. 17 illustrates a side view of a CDM, according to an embodiment of the present invention.

FIG. 17 illustrates a side view of a CDM, according to an embodiment of the present invention. FIG. 17 shows an embodiment in which the cutting tool is installed before bending motion, because its diameter is greater than or equal to the tool channel of the steerable mechanism. This approach is used during drilling applications to minimize buckling and vibration, because the cutting tool is directly attached to the steerable body.

Figure 18:
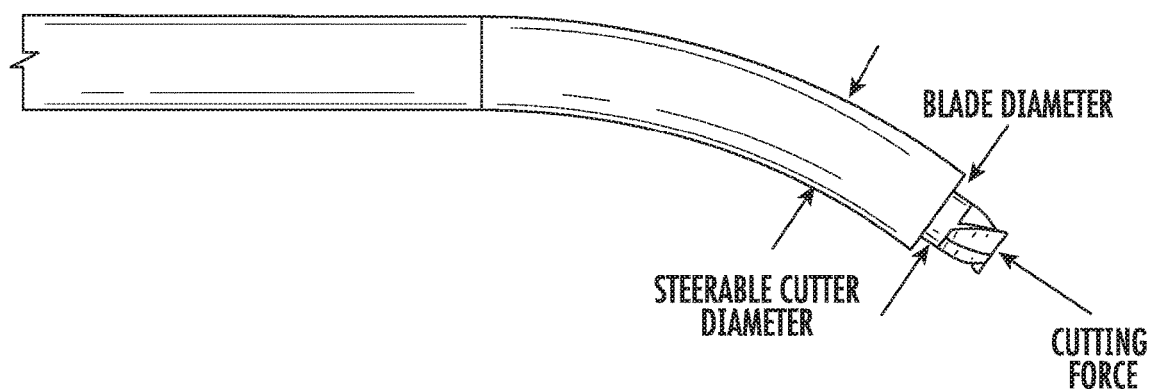
FIG. 18 illustrates a side view of a CDM, according to an embodiment of the present invention.

FIG. 18 illustrates a side view of a CDM, according to an embodiment of the present invention. FIG. 18 shows an embodiment in which the flexible cutting tool passes through the tool channel of the steerable cutter and its diameter is less than diameter of the tool channel. This type of cutting tool can be used for shaving or milling the surface of the bone and can be changed during the bending motion of the steerable mechanism.

Figure 19:
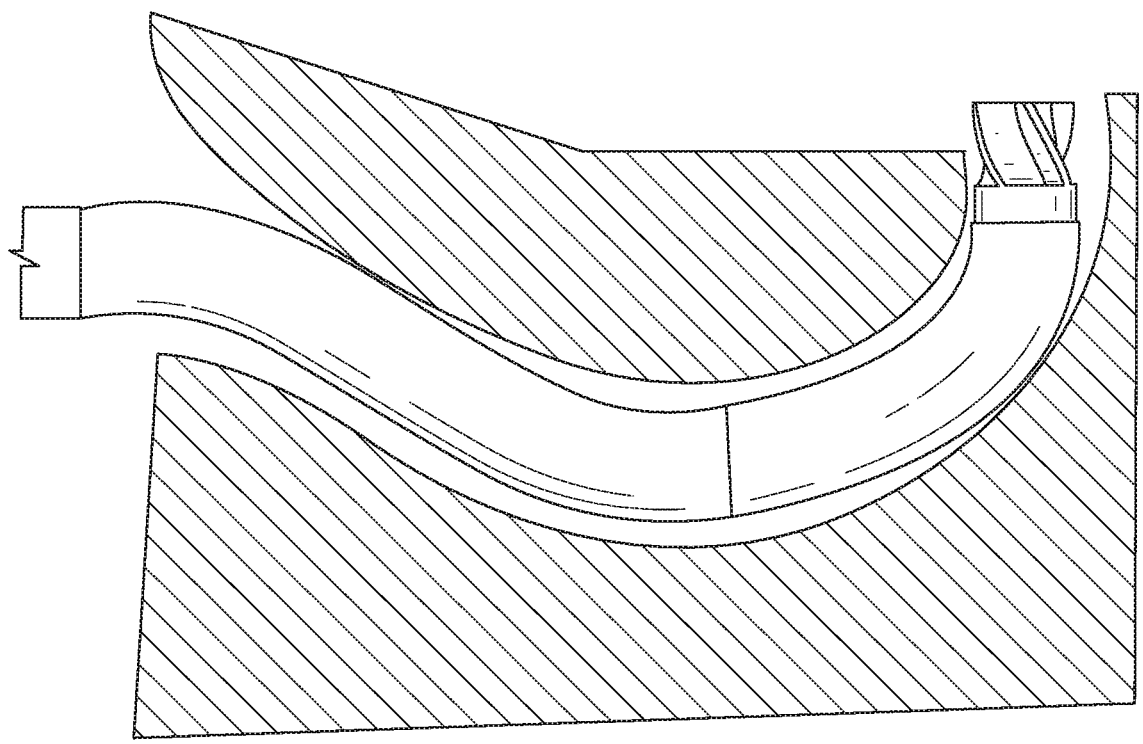
FIG. 19 illustrates a side view of a CDM cutting through a curved path, without buckling, according to an embodiment of the present invention.

Common cutting tools such as drills use rigid drill bits or milling blades to transfer transmitted torque to the cutter blade. Also, rigidity of the cutting blade is a requirement to avoid buckling because of cutting forces. The rigid cutting tools may have limitation in reaching areas such as what is shown in FIG. 19. The device of the present invention, however, can have insertion and flexible bending motion for steering through desired path while avoiding obstacles. Also, it can offer sufficient mechanical rigidity to prevent buckling during the cutting/milling procedure. FIG. 19 illustrates a side view of a CDM cutting through a curved path, without buckling, according to an embodiment of the present invention.

The use of a cable driven mechanism for active control of the steerable mechanism's shape. This feature reduces the size of the device and its cost. Lubrication and debris removal is one important parameter for most of the cutting applications. Especially when the cutting point is not accessible. Furthermore, the lumen defined by the CDM can be used for passing endoscopes, cameras or other tools inside the cutting channel.

Avoiding buckling is necessary for drilling tasks. Minimizing vibration is also necessary, especially for milling purposes. Proposed device can provide both features considering the steerable mechanism. Active sweeping during milling process is another useful feature of this cutter.

Figure 20A:
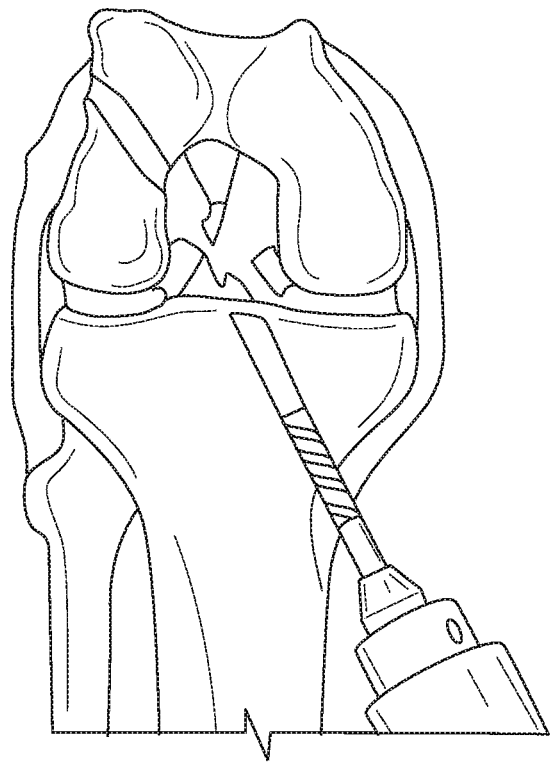
FIGS. 20A and 20B illustrate possible applications of the steerable device of the present invention.
Figure 20B:
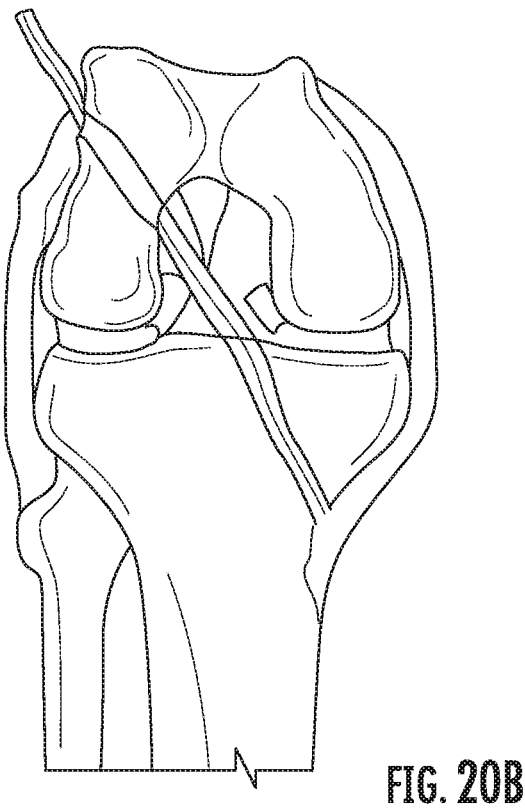

FIGS. 20A and 20B illustrate possible applications of the steerable device of the present invention. Core decompression using the device of the present invention is shown in FIG. 20A and ACL reconstruction is shown in FIG. 20B.

Control of the device of the present invention or display of visual images or data related to the device and procedure of the present invention can be carried out using a computer, non-transitory computer readable medium, or alternately a computing device or non-transitory computer readable medium incorporated into the robotic device or the imaging device. Visual displays may include images from associated endoscopic cameras used in conjunction with the device or image guidance of the device within the surgical field.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out control or displays associated with a device of the present invention. The computing device can also take the form of an operating console computer. The operating console is a non-generic computer specifically designed by the manufacturer. It is not a standard business or personal computer that can be purchased at a local store. Additionally, the console computer can carry out communications with any associated imaging modality through the execution of proprietary custom built software that is designed and written by the manufacturer for the computer hardware to specifically operate the hardware.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A drilling device comprising:
a steerable mechanism comprising a flexible portion with a controllable bending angle, wherein the steerable mechanism further comprises a flexible cable configured to actuate the controllable bending angle, and wherein the steerable mechanism defines an inner lumen, and wherein the steerable mechanism includes a steering motor configured to apply pulling force on the cable to achieve the controllable bending angle, and a rotational motor configured to rotate the steerable mechanism about a central axis;
a cutting tool configured to be disposed through the inner lumen of the steerable mechanism;
a cutting motor configured to rotate the cutting tool; and
a driving mechanism comprising a controller configured to provide control of the controllable bending angle of the steerable mechanism, wherein the controller measures and controls a trajectory of the steerable mechanism via tension in the flexible cable, and wherein the controller measures and controls feed velocity.

2. The drilling device of claim 1 wherein the driving mechanism comprises a housing.

3. The drilling device of claim 2 wherein a battery is disposed within the housing of the driving mechanism.

4. The drilling device of claim 1 wherein the driving mechanism includes a switch for engaging a rotational drilling action of the steerable mechanism.

5. The drilling device of claim 1 wherein the controller comprises one selected from a group consisting of a joystick and directional buttons.

6. The drilling device of claim 1 further comprising robotic control of the steerable mechanism.

7. The drilling device of claim 1 wherein the driving mechanism includes a control for speed of the rotational drilling action of the steerable mechanism.

8. The drilling device of claim 1 wherein the steerable mechanism comprises a continuum dexterous manipulator (CDM) or a multi-back bone jointed mechanism with an open lumen.

9. The drilling device of claim 8 further comprising the CDM being formed from a metal.

10. The drilling device of claim 9 wherein the metal comprises one selected from a group consisting of titanium or nitinol.

11. The drilling device of claim 1 wherein the controllable bending angle is controlled by pulling on the flexible cable or controlling the controllable bending angle.

12. The drilling device of claim 1 wherein the steerable mechanism defines a second lumen through which an endoscope can be disposed.

13. The drilling device of claim 1 wherein the cutting tool comprises a ball end-mill or other types of milling, drilling, and machining geometries.

14. The drilling device of claim 1 wherein the steerable mechanism further comprises notches cut along its length to facilitate bending.

15. The drilling device of claim 1 wherein the steerable mechanism defines a plurality of channels through which a plurality of flexible cables are disposed for control of the steerable mechanism.

16. The drilling device of claim 15 wherein the plurality of cables are actuated to provide movement of the steerable mechanism.

17. The drilling device of claim 1 wherein the cutting tool comprises a flexible distal end.

18. The drilling device of claim 1 wherein the cutting tool is formed from a metal.

19. The drilling device of claim 1 wherein the cutting tool comprises a quick connect mechanism.

20. The drilling device of claim 1 wherein the controller is configured to execute a preoperative trajectory plan.

21. The drilling device of claim 1 wherein the flexible portion comprises a flexible torque coil.

\* \* \* \* \*